US008882658B2

(12) United States Patent
Sakai et al.

(10) Patent No.: US 8,882,658 B2
(45) Date of Patent: Nov. 11, 2014

(54) ENDOSCOPE SYSTEM

(71) Applicant: Olympus Medical Systems Corp., Tokyo (JP)

(72) Inventors: Yuji Sakai, Hachioji (JP); Tsutomu Uzawa, Hidaka (JP); Katsumi Hirakawa, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/050,789

(22) Filed: Oct. 10, 2013

(65) Prior Publication Data

US 2014/0088363 A1    Mar. 27, 2014

Related U.S. Application Data

(63) Continuation of application No. PCT/JP2013/060188, filed on Apr. 3, 2013.

(30) Foreign Application Priority Data

Jun. 1, 2012    (JP) ................................. 2012-126422

(51) Int. Cl.
*A61B 1/07*  (2006.01)
*A61B 1/00*  (2006.01)
*A61B 1/06*  (2006.01)

(52) U.S. Cl.
CPC ......... *A61B 1/00057* (2013.01); *A61B 1/00009* (2013.01); *A61B 1/0638* (2013.01); *A61B 1/00165* (2013.01); *A61B 1/00006* (2013.01); *A61B 1/00172* (2013.01); *A61B 1/06* (2013.01)
USPC ............ 600/118; 600/103; 600/173; 600/182

(58) Field of Classification Search
CPC ........... A61B 1/00172; A61B 1/00057; A61B 1/0009; A61B 1/07; A61B 1/06; A61B 5/0062; G02B 21/0064; G02B 21/0072

USPC .......................... 600/103, 118, 160, 173, 182
See application file for complete search history.

(56) References Cited

U.S. PATENT DOCUMENTS 7,338,439 B2 *  3/2008  Kanai ........................... 600/176
8,040,412 B2 * 10/2011  Yamamoto .................... 348/273
(Continued)

FOREIGN PATENT DOCUMENTS

EP   2 083 572 A1   7/2009
JP   2009-10674 A   1/2009
(Continued)

OTHER PUBLICATIONS

Japanese Office Action dated Nov. 19, 2013 in corresponding Japanese Patent Application No. 2013-544047.

*Primary Examiner* — John P Leubecker
(74) *Attorney, Agent, or Firm* — Scully, Scott, Murphy & Presser, PC

(57) ABSTRACT

An endoscope system includes: an endoscope that has a light guiding member that guides an illuminating light, an optical system that irradiates the illuminating light onto an object, and a drive portion that rocks the light guiding member so that the illuminating light is irradiated along a predetermined scanning pattern; a coordinate information acquisition portion that can identify an irradiation position; a storage portion in which information regarding chromatic aberration of magnification caused by the optical system, is previously stored a correction information acquisition portion that, upon detecting that light of the predetermined wavelength band is irradiated onto a position corresponding to a predetermined image height, detects an aberration amount of the light of the other wavelength band and outputs image correction information that corrects chromatic aberration of magnification based on the aberration amount; and an image processing portion that performs image correction processing based on the image correction information.

4 Claims, 8 Drawing Sheets

(56) References Cited

U.S. PATENT DOCUMENTS

| | | | |
|---|---|---|---|
| 8,305,432 B2* | 11/2012 | Johnston | 348/65 |
| 8,446,477 B2* | 5/2013 | Irisawa et al. | 348/208.11 |
| 2005/0052753 A1* | 3/2005 | Kanai | 359/642 |
| 2008/0165360 A1* | 7/2008 | Johnston | 356/394 |
| 2009/0190008 A1* | 7/2009 | Kasahara | 348/242 |
| 2010/0168515 A1* | 7/2010 | Sugimoto | 600/109 |
| 2013/0003131 A1* | 1/2013 | Johnston | 358/406 |
| 2013/0076879 A1* | 3/2013 | On | 348/65 |

FOREIGN PATENT DOCUMENTS

| | | |
|---|---|---|
| JP | 2009-177704 A | 8/2009 |
| JP | 2010-148769 A | 7/2010 |
| JP | 2011-101665 A | 5/2011 |
| JP | 2011182202 A | 9/2011 |
| JP | 2011-217836 A | 11/2011 |
| JP | 2012-15781 A | 1/2012 |

* cited by examiner

IMAGE SURFACE

OBJECT SURFACE

US 8,882,658 B2

ENDOSCOPE SYSTEM

CROSS REFERENCE TO RELATED APPLICATION

This application is a continuation application of PCT/JP2013/060188 filed on Apr. 3, 2013 and claims benefit of Japanese Application No. 2012-126422 filed in Japan on Jun. 1, 2012, the entire contents of which are incorporated herein by this reference.

BACKGROUND OF THE INVENTION

1. Field of the Invention

The present invention relates to an endoscope system, and more particularly to an endoscope system that scans an object and acquires an image.

2. Description of the Related Art

Various technologies have been proposed with respect to endoscopes used in medical fields in order to narrow the diameter of an insertion portion thereof that is inserted into a body cavity of a subject, to thereby reduce the burden of the subject. As one example of such technology, Japanese Patent Application Laid-Open Publication No. 2011-101665 discloses an optical scanning electronic endoscope that does not have a solid-state image pickup device in a portion corresponding to the aforementioned insertion portion, and an electronic endoscope system that includes the optical scanning electronic endoscope.

More specifically, Japanese Patent Application Laid-Open Publication No. 2011-101665 discloses an electronic endoscope system having a configuration in which an object is scanned according to a previously set scanning pattern (for example, in a spiral shape) by causing a distal end portion of an illuminating fiber that guides an illuminating light that is emitted from a light source portion to perform a resonating movement, return light from the object is received by a light receiving fiber that is disposed around the illuminating fiber, and an image of the object is generated using signals obtained by splitting the return light that was received by the light receiving fiber into respective color components thereof.

Further, as a calibration method for chromatic aberration of magnification that occurs in the aforementioned electronic endoscope system, Japanese Patent Application Laid-Open Publication No. 2011-101665 also discloses a calibration method that uses an orange component that is detected in accordance with a light amount of orange light emitted from a light source portion to correct a red component that is detected in accordance with a light amount of red light that is emitted from the light source portion.

SUMMARY OF THE INVENTION

An endoscope system according to one aspect of the present invention includes: an endoscope having a light guiding member that guides an illuminating light that is emitted from a light source, an optical system that irradiates the illuminating light that is guided by the light guiding member onto an object, and a drive portion that rocks the light guiding member so that an irradiation position of the illuminating light that is irradiated onto the object through the optical system is an irradiation position along a predetermined scanning pattern; a coordinate information acquisition portion that acquires coordinate information that can identify an irradiation position of the illuminating light that is irradiated along the predetermined scanning pattern; a storage portion in which optical characteristics information is previously stored that, in a case where light of a predetermined wavelength band is set as a standard of chromatic aberration of magnification that is caused by the optical system, shows a correlation between an image height and an aberration amount of light of another wavelength band; a correction information acquisition portion that, upon detecting that the light of the predetermined wavelength band is irradiated onto a position corresponding to a predetermined image height based on the coordinate information, detects an aberration amount of the light of the other wavelength band at the predetermined image height based on the optical characteristics information that is stored in the storage portion, and outputs image correction information that corrects chromatic aberration of magnification of an image that is generated in accordance with return light of the light of the other wavelength band based on the aberration amount; and an image processing portion that performs image correction processing based on the image correction information.

DETAILED DESCRIPTION OF THE PREFERRED EMBODIMENT

An embodiment of the present invention is described hereunder with reference to the drawings.

Figure 1:
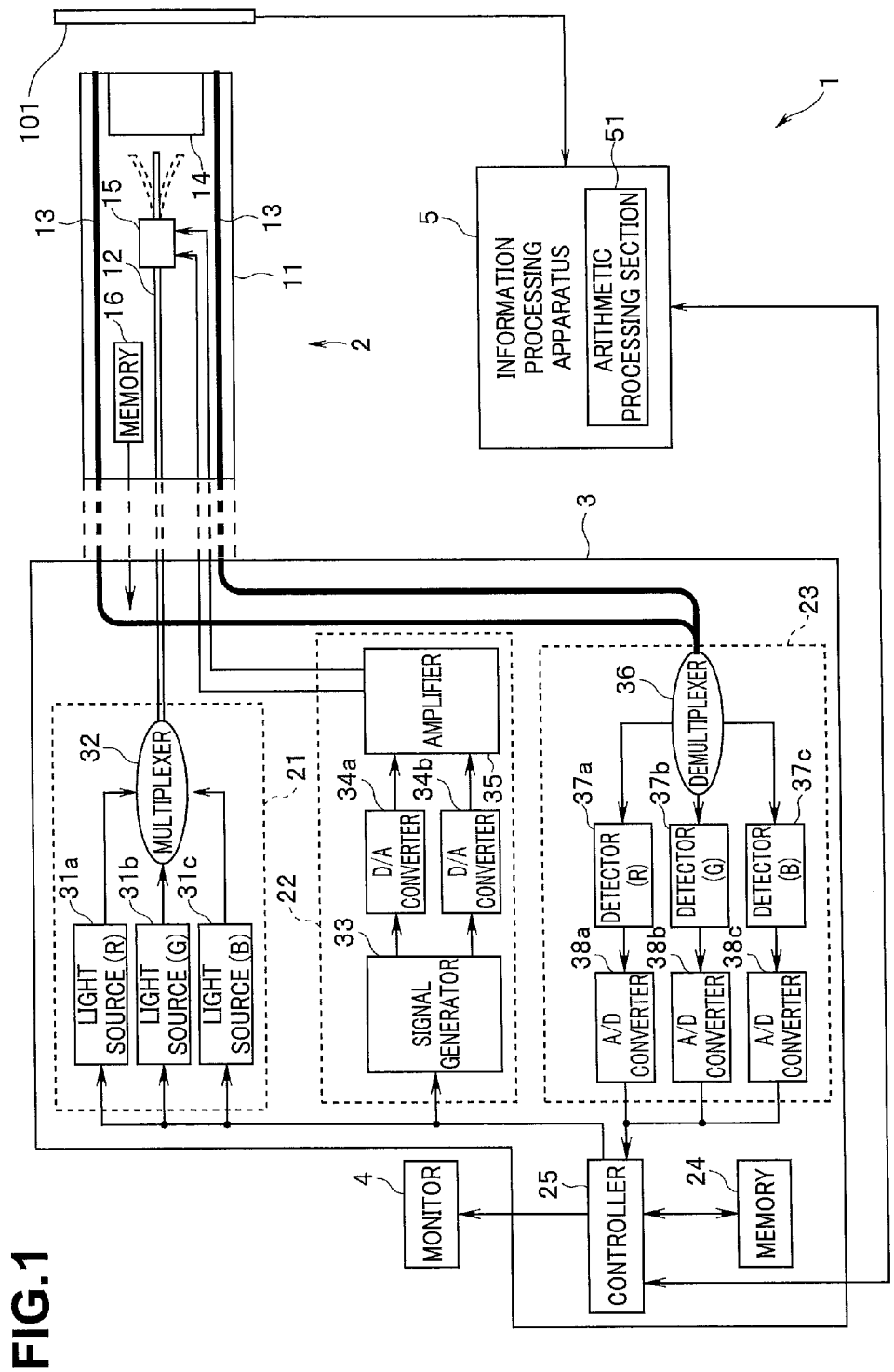
FIG. 1 is a view illustrating the configuration of principal parts of an endoscope system according to an embodiment of the present invention.

FIG. 1 to FIG. 11 relate to an embodiment of the present invention. FIG. 1 is a view illustrating the configuration of principal parts of an endoscope system according to the embodiment of the present invention.

As shown in FIG. 1, an endoscope system 1 includes, for example, a scanning endoscope 2 that is inserted into a body cavity of a subject, a main body apparatus 3 that is connected to the endoscope 2, a monitor 4 that is connected to the main body apparatus 3, and an information processing apparatus 5 that is connected to the main body apparatus 3.

The endoscope 2 is configured to have an insertion portion 11 having flexibility that is formed in an elongated shape that can be inserted into a body cavity of a subject. Note that an unshown connector or the like for detachably connecting the endoscope 2 to the main body apparatus 3 is provided at a proximal end portion of the insertion portion 11.

An illuminating fiber 12 having a function as a light guiding member that guides illuminating light supplied from a light source unit 21 of the main body apparatus 3 to an objective optical system 14, and a light receiving fiber 13 that receives return light from an object and guides the return light to a detection unit 23 of the main body apparatus 3 are respectively inserted through a part that extends from the proximal end portion to a distal end portion inside the insertion portion 11.

An end portion including a light entering face of the illuminating fiber 12 is disposed at a multiplexer 32 that is provided inside the main body apparatus 3. Further, an end portion including a light exiting face of the illuminating fiber 12 is disposed in a state in which the end portion is not fixed by a fixing member or the like in the vicinity of a light entering face of the objective optical system 14 provided at a distal end portion of the insertion portion 11. That is, illuminating light that is guided by the illuminating fiber 12 is irradiated onto an object through the objective optical system 14.

Note that, in the present embodiment, as a design value that corresponds to design data of the objective optical system 14 that is described later, it is desirable that, for example, a numerical aperture NA of the end portion including the light exiting face of the illuminating fiber 12 is set to 0.0963.

The end portion including the light entering face of the light receiving fiber 13 is fixedly disposed around the light exiting face of the objective optical system 14 at the distal end face of the distal end portion of the insertion portion 11. The end portion including the light exiting face of the light receiving fiber 13 is disposed at a demultiplexer 36 that is provided inside the main body apparatus 3.

An actuator 15 that drives based on driving signals outputted from a driver unit 22 of the main body apparatus 3 is mounted at a midway portion of the illuminating fiber 12 on the distal end portion side of the insertion portion 11.

Figure 2:
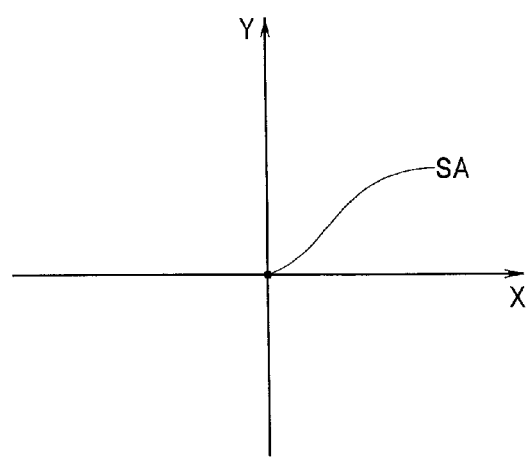
FIG. 2 is a view illustrating an example of a virtual XY plane that is set on a surface of an object.

In the following description, an example is described of a case where, as a virtual plane that is perpendicular to an insertion axis (or optical axis of the objective optical system 14) corresponding to an axis in a longitudinal direction of the insertion portion 11, an XY plane as shown in FIG. 2 is set on the surface of an object. FIG. 2 is a view that illustrates an example of a virtual XY plane that is set on the surface of an object.

More specifically, in a case where the insertion axis of the insertion portion 11 is virtually set as existing in a direction that corresponds to a direction from the front side of the paper surface to the inner side, a point SA on the XY plane in FIG. 2 indicates a point of intersection between the insertion axis and the paper surface. The X-axis direction in the XY plane in FIG. 2 is set as the direction from the left side of the paper surface towards the right side thereof. The Y-axis direction in the XY plane in FIG. 2 is set as the direction from the lower side of the paper surface to the upper side thereof. Further, the X-axis and Y-axis that constitute the XY plane in FIG. 2 intersect at the point SA.

The actuator 15 includes an X-axis actuator (not shown) that operates so as to rock the end portion including the light exiting face of the illuminating fiber 12 in the X-axis direction based on a first driving signal that is outputted from the driver unit 22 of the main body apparatus 3, and a Y-axis actuator (not shown) that operates so as to rock the end portion including the light exiting face of the illuminating fiber 12 in the Y-axis direction based on a second driving signal that is outputted from the driver unit 22 of the main body apparatus 3. Accompanying the aforementioned operations of the X-axis actuator and the Y-axis actuator, the end portion including the light exiting face of the illuminating fiber 12 is rocked in a spiral shape that is centered on the point SA.

Note that, in the present embodiment, as a design value that corresponds to design data of the objective optical system 14 that is described later, it is desirable that, for example, the length (of the end portion including the light exiting face) of the illuminating fiber 12 that is rocked by the actuator 15 is set to 3.4 mm.

A memory 16 in which endoscope information including various kinds of information relating to the endoscope 2 such as, for example, optical characteristics information that is determined in accordance with the characteristics of the objective optical system 14 is previously stored is provided in the insertion portion 11. The endoscope information stored in the memory 16 is read out by a controller 25 of the main body apparatus 3 when the endoscope 2 and the main body apparatus 3 are connected. Note that details of the optical characteristics information of the objective optical system 14 that is stored in the memory 16 are described later.

Figure 3:
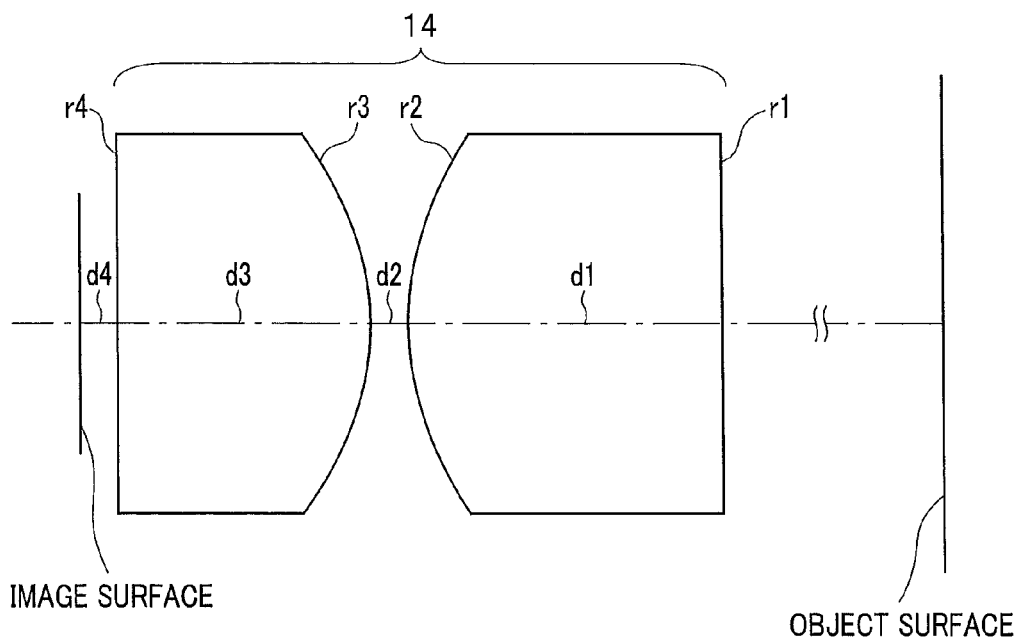
FIG. 3 is a view illustrating an example of the configuration of an objective optical system that is provided in an endoscope.
Figure 4:
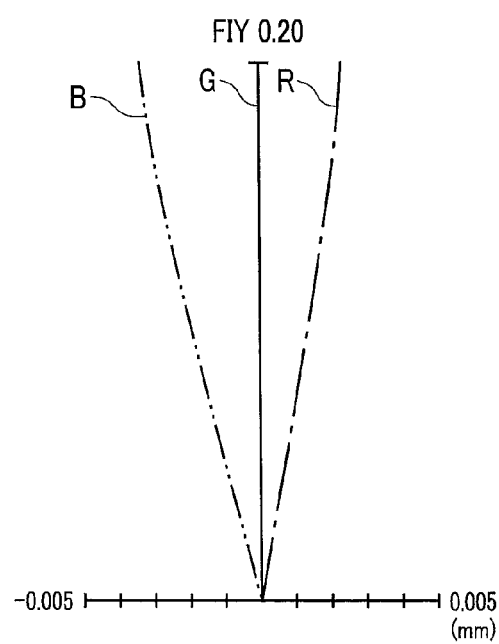
FIG. 4 is an aberration diagram illustrating chromatic aberration of magnification that occurs in the objective optical system shown in FIG. 3.

An example of the specific configuration of the objective optical system 14 provided in the distal end portion of the insertion portion 11 will now be described referring to FIG. 3 and FIG. 4. FIG. 3 is a view that illustrates an example of the configuration of the objective optical system provided in the endoscope according to the present embodiment. FIG. 4 is an aberration diagram that illustrates chromatic aberration of magnification that occurs in the objective optical system shown in FIG. 3.

As shown in FIG. 3, the objective optical system 14, for example, is formed of two plano-convex lenses having positive refractive power. The objective optical system 14 of the present embodiment is designed in accordance with the design data described below.

Note that, in the following design data of the objective optical system 14, reference character r represents the radius of curvature, reference character d represents the inter-surface spacing, reference character nd represents the refractive index for the d-line (587.6 nm) of each lens, and reference character vd represents the Abbe number on the d-line of each lens. Further, in the design data of the objective optical system 14 described hereunder, the symbol "∞" for the radius of curvature r indicates infinity, and D=7.50 (mm) with respect to "object surface" in the surface number column indicates the focal position of the objective optical system 14. The unit of data relating to distance such as the radius of curvature r and the inter-surface spacing d is assumed to be millimeters (mm) unless otherwise stated. In addition, it is assumed that the term "object surface" in the following design data of the objective optical system 14 and in FIG. 3 refers to the surface of an observation target. Further, it is assumed the term "image surface" in the following design data of the objective optical system 14 and in FIG. 3 refers to a virtual surface onto which the track of the light exiting face of the illuminating fiber 12 that is rocked in a spiral shape is projected.

(Design Data)

| Surface number | r | d | nd | vd |
| --- | --- | --- | --- | --- |
| Object surface | ∞ | 7.50 | | |
| 1 | ∞ | 0.50 | 1.89019 | 40.76 |
| 2 | −0.5100 | 0.06 | | |
| 3 | 0.4750 | 0.40 | 1.89019 | 40.76 |
| 4 | ∞ | 0.06 | | |
| Image surface | ∞ | | | |

In the objective optical system 14 designed in accordance with the above described design data, chromatic aberration of magnification as illustrated, for example, in FIG. 4 arises.

Note that an alternate long and short dash line in FIG. 4 shows a correlation between the image height (corresponds to "FIY" in FIG. 4) of light of a red wavelength band (hereunder, also referred to as "R light") and an aberration amount thereof caused by chromatic aberration of magnification when taking light of a green wavelength band (hereunder, also referred to as "G light") as a standard (when the chromatic aberration of magnification of G light is defined as being equal to 0). Further, an alternate long and two short dashes line in FIG. 4 shows the correlation between the image height of light of a blue wavelength band (hereunder, also referred to as "B light") and an aberration amount thereof caused by chromatic aberration of magnification when taking the G light as a standard. Further, a maximum image height that corresponds to the maximum value of "FIY" in FIG. 4 is a value that roughly matches a distance (for example, 0.2 (mm)) from the point SA on the surface of the object to a point YMAX that is described later, and is a value that is determined in accordance with a maximum amplitude of the illuminating fiber 12 that is rocked by the actuator 15.

That is, the above described design data and data that shows the correlation between aberration amounts and image heights of R light and B light in a case where G light is set as a standard for chromatic aberration of magnification that is caused by the objective optical system 14, as exemplified by the aberration diagram in FIG. 4, are stored together in the memory 16 of the insertion portion 11 as optical characteristics information that is determined in accordance with the characteristics of the objective optical system 14.

The main body apparatus 3 is configured to have the light source unit 21, the driver unit 22, the detection unit 23, a memory 24, and the controller 25.

The light source unit 21 is configured to have a light source 31a, a light source 31b, a light source 31c, and a multiplexer 32.

The light source 31a, for example, includes a laser light source, and is configured to emit R light to the multiplexer 32 when turned on by control of the controller 25.

The light source 31b, for example, includes a laser light source, and is configured to emit G light to the multiplexer 32 when turned on by control of the controller 25.

The light source 31c, for example, includes a laser light source, and is configured to emit B light to the multiplexer 32 when turned on by control of the controller 25.

The multiplexer 32 is configured to be capable of multiplexing the R light emitted from the light source 31a, the G light emitted from the light source 31b, and the B light emitted from the light source 31c, and supplying the multiplexed light to the light entering face of the illuminating fiber 12.

The driver unit 22 is configured to have a signal generator 33, digital-to-analog (hereunder, referred to as "D/A") converters 34a and 34b, and an amplifier 35.

Figure 5:
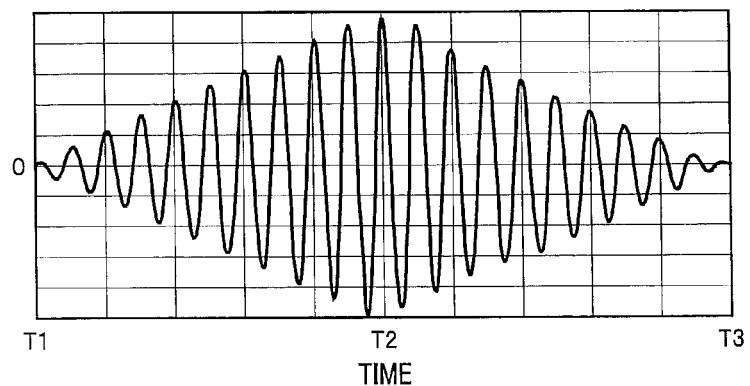
FIG. 5 is a view illustrating an example of a signal waveform of a first driving signal that is supplied to an actuator provided in the endoscope.

The signal generator 33 is configured to generate a signal of a predetermined wavelength, for example, as shown in FIG. 5, as a first driving signal that causes the end portion including the light exiting face of the illuminating fiber 12 to rock in the X-axis direction and to output the generated signal to the D/A converter 34a, based on control of the controller 25. FIG. 5 is a view illustrating an example of the signal waveform of the first driving signal that is supplied to the actuator provided in the endoscope.

Figure 6:
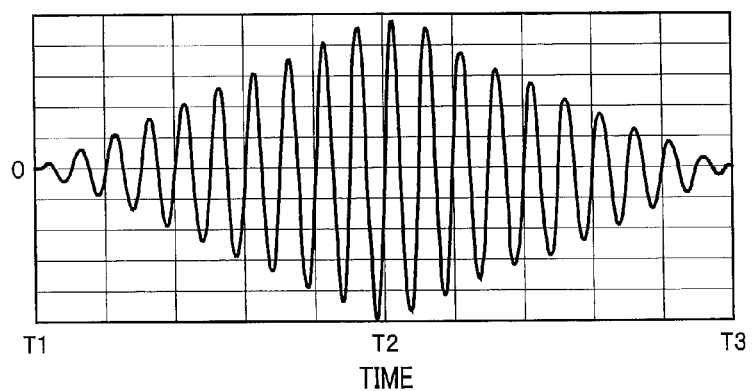
FIG. 6 is a view illustrating an example of a signal waveform of a second driving signal that is supplied to the actuator provided in the endoscope.

The signal generator 33 is also configured to generate a signal of a waveform whose phase is shifted by 90° relative to the phase of the aforementioned first driving signal, for example, as shown in FIG. 6, and output the generated signal to the D/A converter 34b as a second driving signal that causes the end portion including the light exiting face of the illuminating fiber 12 to rock in the Y-axis direction, based on control of the controller 25. FIG. 6 is a view illustrating an example of the signal waveform of the second driving signal that is supplied to the actuator provided in the endoscope.

The D/A converter 34a is configured to convert the digital first driving signal that was outputted from the signal generator 33 to an analog first driving signal, and output the analog first driving signal to the amplifier 35.

The D/A converter 34b is configured to convert the digital second driving signal that was outputted from the signal generator 33 to an analog second driving signal, and output the analog second driving signal to the amplifier 35.

The amplifier 35 is configured to amplify the first and second driving signals that were outputted from the D/A converters 34a and 34b, and output the amplified first and second driving signals to the actuator 15.

In this case, an amplitude value (signal level) of the first driving signal that is exemplified in FIG. 5 gradually increases when a time T1 at which the amplitude value is a minimum value is taken as a starting point, gradually decreases after reaching a maximum value at a time T2, and becomes the minimum value again at a time T3.

Further, an amplitude value (signal level) of the second driving signal that is exemplified in FIG. 6 gradually increases when the time T1 at which the amplitude value is a minimum value is taken as a starting point, gradually decreases after reaching a maximum value in the vicinity of the time T2, and becomes the minimum value again at the time T3.

Figure 7A:
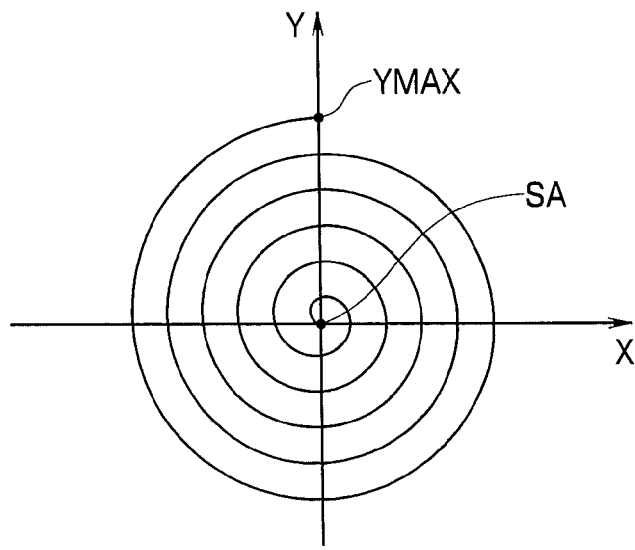
FIG. 7A is a view for describing the temporal displacement of irradiation coordinates of illuminating light from a point SA to a point YMAX in a case where illuminating light is irradiated onto the virtual XY plane shown in FIG. 2.
Figure 7B:
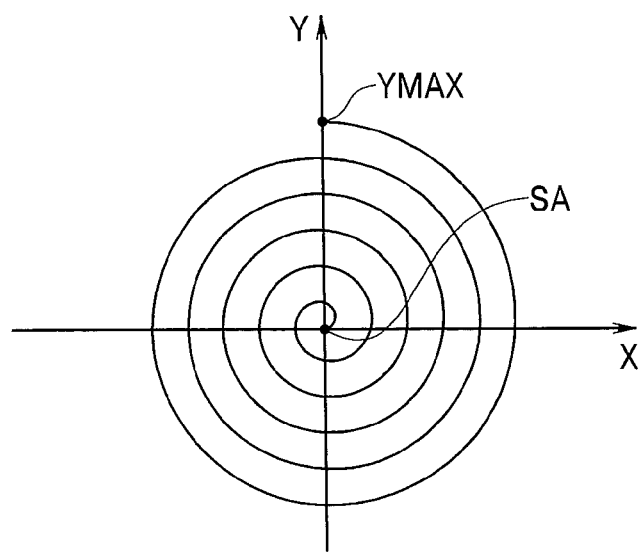
FIG. 7B is a view for describing the temporal displacement of irradiation coordinates of illuminating light from the point YMAX to the point SA in a case where illuminating light is irradiated onto the virtual XY plane shown in FIG. 2.

When the first driving signal shown in FIG. 5 is supplied to the X-axis actuator of the actuator 15 and the second driving signal shown in FIG. 6 is supplied to the Y-axis actuator of the actuator 15, the end portion including the light exiting face of the illuminating fiber 12 rocks in a spiral shape around the point SA, and the surface of the object is scanned in a spiral shape as shown in FIG. 7A and FIG. 7B in accordance with the rocking. FIG. 7A is a view for describing the temporal displacement of irradiation coordinates of illuminating light from the point SA to the point YMAX when illuminating light is irradiated onto the virtual XY plane as shown in FIG. 2. FIG. 7B is a view for describing the temporal displacement of irradiation coordinates of illuminating light from the point YMAX to the point SA when illuminating light is irradiated onto the virtual XY plane as shown in FIG. 2.

Specifically, at the time T1, illuminating light is irradiated onto a position that corresponds to the point SA on the surface of the object. Thereafter, as the amplitude values of the first and second driving signals increase during the time period from the time T1 to the time T2, the positions of the irradiation coordinates of the illuminating light on the surface of the object change so as to draw a first spiral-shaped track to the outside in a manner that takes the point SA as a starting point, and furthermore, upon reaching the time T2, the illuminating light is irradiated onto the point YMAX that is the outermost point of the irradiation coordinates of the illuminating light on the surface of the object. Subsequently, as the amplitude values of the first and second driving signals decrease during the time period from the time T2 to the time T3, the positions of the irradiation coordinates of the illuminating light on the surface of the object change so as to draw a second spiral-shaped track to the inside in a manner that takes the point YMAX as a starting point, and furthermore, upon reaching the time T3, the illuminating light is irradiated onto the point SA on the surface of the object.

That is, the actuator 15 is configured so that, based on the first and second driving signals that are supplied form the driver unit 22, the end portion including the light exiting face of the illuminating fiber 12 can be rocked so that the irradiation positions of illuminating light that is irradiated onto the object through the objective optical system 14 are irradiation positions along the spiral-shaped scanning patterns exemplified in FIG. 7A and FIG. 7B.

Note that in the present embodiment it is assumed that an image with an angle of view (field of view) of 90° is generated as illuminating light is irradiated through the objective optical system 14 along a spiral shape as shown in FIG. 7A and FIG. 7B and, further, return light from the surface of the object is received by the light receiving fiber 13 that is fixedly disposed around the light exiting face of the objective optical system 14.

The detection unit 23 is configured to have the demultiplexer 36, detectors 37a, 37b, and 37c, and analog-to-digital (hereunder, referred to as "A/D") converters 38a, 38b, and 38c.

The demultiplexer 36 is equipped with a dichroic mirror or the like, and is configured to separate return light emitted from the light exiting face of the light receiving fiber 13 into light of each of the color components of R (red), G (green), and B (blue), and emit the separated light components to the detectors 37a, 37b, and 37c, respectively.

The detector 37a is configured to detect the intensity of the R light that is outputted from the demultiplexer 36, generate an analog R signal in accordance with the detected R light intensity, and output the analog R signal to the A/D convertor 38a.

The detector 37b is configured to detect the intensity of the G light that is outputted from the demultiplexer 36, generate an analog G signal in accordance with the detected G light intensity, and output the analog G signal to the A/D convertor 38b.

The detector 37c is configured to detect the intensity of the B light that is outputted from the demultiplexer 36, generate an analog B signal in accordance with the detected B light intensity, and output the analog B signal to the A/D convertor 38c.

The A/D convertor 38a is configured to convert the analog R signal that was outputted from the detector 37a into a digital R signal, and output the digital R signal to the controller 25.

The A/D convertor 38b is configured to convert the analog G signal that was outputted from the detector 37b into a digital G signal, and output the digital G signal to the controller 25.

The A/D convertor 38c is configured to convert the analog B signal that was outputted from the detector 37c into a digital B signal, and output the digital B signal to the controller 25.

A control program for performing control of the main body apparatus 3 or the like is previously stored in the memory 24. Image correction information that is obtained as a processing result of the information processing apparatus 5 is also stored in the memory 24. Note that the details of the image correction information are described later.

The controller 25 is configured to read out a control program stored in the memory 24, and control the light source unit 21 and the driver unit 22 based on the control program that was read out.

The controller 25 is configured so that endoscope information that is outputted from the memory 16 when the insertion portion 11 is connected to the main body apparatus 3 can be outputted to the information processing apparatus 5.

The controller 25 operates so as to cause image correction information that was outputted from the information processing apparatus 5 to be stored in the memory 24.

The controller 25 is configured to generate an image for a single frame based on an R signal, a G signal and a B signal that are outputted from the detection unit 23 in a time period that is equivalent to the time period from the time T1 to the time T2. Further, the controller 25 is configured to generate an image for a single frame based on an R signal, a G signal and a B signal that are outputted from the detection unit 23 in a time period that is equivalent to the time period from the time T2 to the time T3.

In addition, in a case where image correction information is stored in the memory 24, the controller 25 operates so as to perform image correction processing based on the image correction information with respect to an image of each frame, and cause corrected images that underwent the image correction processing to be displayed on the monitor 4 at a predetermined frame rate.

The information processing apparatus 5 is configured to have an arithmetic processing section 51 that performs processing relating to acquisition of image correction information based on optical characteristics information outputted from the controller 25 and coordinate information outputted from a light irradiation coordinates detection module 101.

In this case, the light irradiation coordinates detection module 101 that is equipped with a function as a coordinate information acquisition portion includes a position sensitive detector (PSD) or the like, and is configured to detect a position when illuminating light that was emitted through the objective optical system 14 is received, and output coordinate information in accordance with the detected position.

Note that it is assumed that in the light irradiation coordinates detection module 101 of the present embodiment, the coordinate position of the point SA on the XY plane that is exemplified in FIG. 2, FIG. 7A, and FIG. 7B is previously set to be (0,0). That is, the coordinate information that is outputted from the light irradiation coordinates detection module 101 is information that indicates a relative coordinate position based on the coordinate position (0,0) of the point SA on the XY plane exemplified in FIG. 2, FIG. 7A, and FIG. 7B.

Consequently, based on coordinate information outputted from the light irradiation coordinates detection module 101 having the above described configuration, the arithmetic processing section 51 can identify irradiation positions of illuminating light irradiated in a spiral shape from the endoscope 2.

Further, the arithmetic processing section 51 is configured to acquire image correction information by performing processing, described later, based on coordinate information outputted from the light irradiation coordinates detection module 101 and optical characteristics information included in endoscope information outputted from the controller 25, and output the acquired image correction information to the controller 25 of the main body apparatus 3.

Next, operations and the like of the respective portions of the endoscope system 1 having the above described configuration are described.

First, a surgeon or the like connects the respective portions of the endoscope 2, the monitor 4, and the information processing apparatus 5 to the main body apparatus 3, disposes the light irradiation coordinates detection module 101 at a position facing the distal end face of the endoscope 2, and sets so that coordinate information that is outputted from the light irradiation coordinates detection module 101 is inputted to the information processing apparatus 5.

Thereafter, when the power of each portion of the endoscope system 1 is turned on, endoscope information stored in the memory 16 of the insertion portion 11 is outputted to the information processing apparatus 5 through the controller 25.

Note that according to the present embodiment a configuration may also be adopted in which ID information which can identify the kind of the endoscope 2 is stored in the memory 16 as endoscope information, and optical characteristics information in accordance with a plurality of kinds of the endoscope 2 is stored in the memory 24. In addition, in this case, a configuration may be adopted in which the controller 25 distinguishes the kind of the endoscope 2 that is connected to the main body apparatus 3 based on ID information outputted from the memory 16, selects optical characteristics information that is suitable for the endoscope 2 in accordance with the result of distinguishing the kind of the endoscope 2, and outputs the selected optical characteristics information to the information processing apparatus 5.

At a timing that is approximately immediately after the endoscope information that was read out from the memory 16 is outputted to the information processing apparatus 5, the controller 25 performs control with respect to the light source unit 21 to switch the light source 31b from an "off" to "on" state while keeping the light sources 31a and 31c in an "off" state, and also performs control with respect to the driver unit 22 to cause the driver unit 22 to output the first and second driving signals to the actuator 15. As a result of this control by the controller 25, G light is irradiated in a spiral shape onto the surface of the light irradiation coordinates detection module 101, and coordinate information corresponding to the coordinate positions at which the G light irradiated in the spiral shape was received is sequentially outputted from the light irradiation coordinates detection module 101.

Upon detecting that one item of coordinate information that corresponds to a predetermined image height of the G light was outputted from the light irradiation coordinates detection module 101, the arithmetic processing section 51 that is equipped with a function as a correction information acquisition portion detects an aberration amount of the R light and the B light at the predetermined image height, respectively, based on the optical characteristics information, and performs processing to acquire R image correction information to be used in correction processing of an R image that is generated in accordance with irradiation of the R light, and B image correction information to be used in correction processing of a B image that is generated in accordance with irradiation of the B light, respectively, based on the respective aberration amounts that are detected.

Specifically, for example, upon detecting that one item of coordinate information that corresponds to a predetermined image height of the G light was outputted from the light irradiation coordinates detection module 101, the arithmetic processing section 51 detects the aberration amount of the R light at the predetermined image height based on the aberration diagram shown in FIG. 4, calculates a proportion P (%) that the detected aberration amount of the R light occupies with respect to the maximum image height, and acquires the value of the calculated proportion P (%) as R image correction information. Further, for example, upon detecting that one item of coordinate information corresponding to the predetermined image height of the G light was outputted from the light irradiation coordinates detection module 101, the arithmetic processing section 51 detects the aberration amount of the B light at the predetermined image height based on the aberration diagram shown in FIG. 4, calculates a proportion Q (%) that the detected aberration amount of the B light occupies with respect to the maximum image height, and acquires the value of the calculated proportion Q (%) as B image correction information.

The arithmetic processing section 51 outputs the R image correction information and the B image correction information acquired as described above to the controller 25.

Upon detecting that the R image correction information and the B image correction information were outputted from the information processing apparatus 5, the controller 25 stores the respective items of image correction information in the memory 24 and also performs controls with respect to the light source unit 21 to switch the light sources 31a and 31c from an "off" state to an "on" state while keeping the light source 31b in an "on" state. As a result of this control by the controller 25, mixed light that includes R light, G light, and B light is irradiated in a spiral shape onto the surface of an arbitrary object (such as the light irradiation coordinates detection module 101), return light of the mixed light that was irradiated onto the surface of the arbitrary object is received by the light receiving fiber 13, and respective color signals (R signal, G signal, and B signal) that are in accordance with the received return light are sequentially outputted from the detection unit 23.

The controller 25 generates an R image in accordance with the R signal outputted from the detection unit 23, and performs image correction processing that is based on the R image correction information stored in the memory 24 with respect to the generated R image. The controller 25 also generates a B image in accordance with the B signal outputted from the detection unit 23, and performs image correction processing that is based on the B image correction information stored in the memory 24 with respect to the generated B image.

Specifically, as the aforementioned image correction processing, for example, the controller 25 performs processing to contract the R image that was generated in accordance with the R signal outputted from the detection unit 23 by P (%) that corresponds to the proportion of the R image correction information that was stored in the memory 24. Further, as the aforementioned image correction processing, for example, the controller 25 performs processing to expand the B image that was generated in accordance with the B signal outputted from the detection unit 23 by Q (%) that corresponds to the proportion of the B image correction information that was stored in the memory 24.

Further, the controller 25 synthesizes, for each frame, the corrected R image and B image that each underwent the image correction processing and the G image that was generated in accordance with the G signal outputted from the detection unit 23, and displays the synthesized images on the monitor 4 at a predetermined frame rate.

Note that the present embodiment is not limited to a configuration that acquires R image correction information and B image correction information on the basis of G light (the chromatic aberration of magnification of the G light is defined as being equal to 0), but for example a configuration may also be adopted so as to acquire G image correction information to be used for correction processing of a G image and B image correction information on the basis of R light (the chromatic aberration of magnification of the R light is defined as being equal to 0). Further, in the present embodiment a configuration may be adopted so as to acquire R image correction information and G image correction information on the basis of B light (the chromatic aberration of magnification of the B light is defined as being equal to 0).

As described above, according to the present embodiment, on the basis of the aforementioned optical characteristics information and coordinate information that is detected when light of a predetermined single color component is irradiated onto the surface of the light irradiation coordinates detection module 101, information for correcting chromatic aberration of magnification that arises accompanying irradiation of light of other color components that are different to the predetermined single color component can be acquired. As a result, according to the present embodiment, chromatic aberration of magnification that arises when acquiring an image using a scanning endoscope can be corrected more easily than heretofore.

Further, according to the present embodiment, chromatic aberration of magnification that arises in the objective optical system 14 that includes only an optical member having a positive refractive power can be corrected by image correction processing. As a result, according to the present embodiment a color shift that is caused by chromatic aberration of magnification can be corrected while simplifying the configuration of a distal end portion of an insertion portion in a scanning endoscope.

Figure 8:
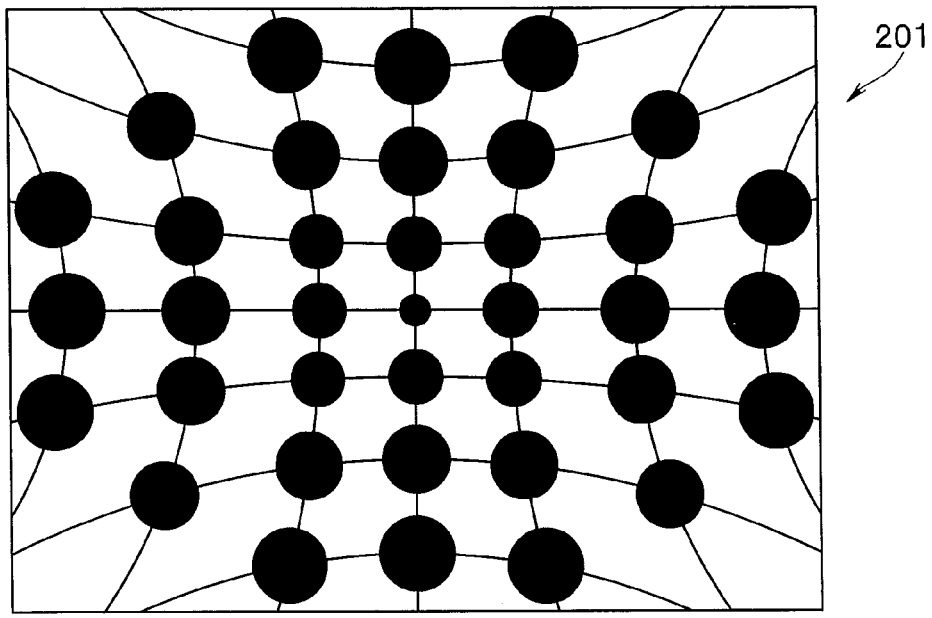
FIG. 8 is a view illustrating an example of a calibration chart that can be utilized when performing image correction processing.

Note that according to the present embodiment, for example, in a case where information such as an aberration diagram that can identify the distortion aberration of the objective optical system 14 is included in optical characteristics information, image correction processing may be performed using a calibration chart 201 as shown in FIG. 8 instead of the light irradiation coordinates detection module 101. FIG. 8 is a view showing an example of a calibration chart that can be utilized when performing image correction processing.

The calibration chart 201 is constructed so as to be suitable for the objective optical system 14 that has barrel distortion aberration, and as shown in FIG. 8, includes a dot pattern formed of a plurality of dots that are drawn in black inside a region with a white background.

Note that the respective dots included in the dot pattern shown in FIG. 8 are drawn so that the diameters of the dots increase in accordance with the proximity of the dots to an outer edge portion from the center portion of the calibration chart 201, and spaces between the dots widen in accordance with the proximity of the dots to the outer edge portion from the center portion of the calibration chart 201.

Figure 9:
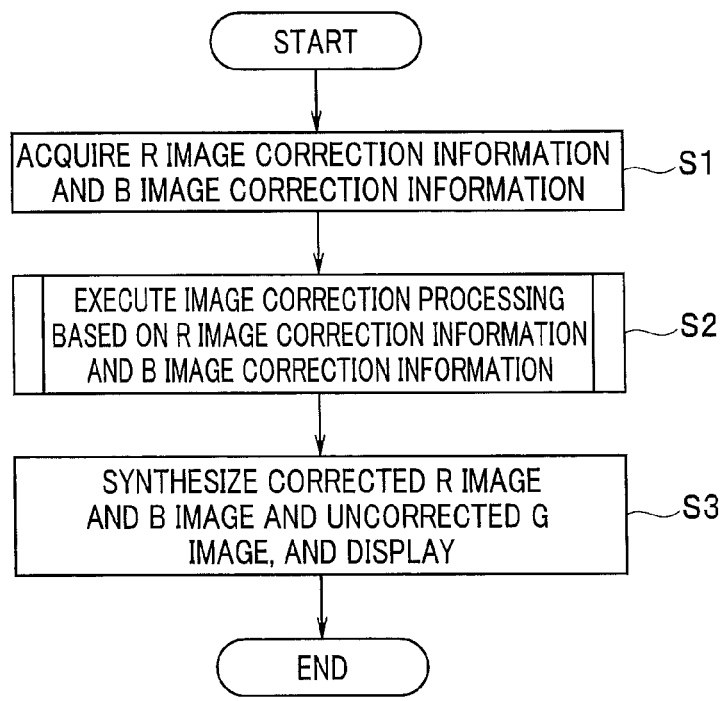
FIG. 9 is a flowchart for describing an outline of processing that is performed using the calibration chart shown in FIG. 8.

Image correction processing and the like that uses this calibration chart 201 will now be described. FIG. 9 is a flowchart for describing an outline of processing that is performed using the calibration chart shown in FIG. 8.

First, a surgeon or the like connects the respective portions of the endoscope 2, the monitor 4, and the information processing apparatus 5 to the main body apparatus 3. The surgeon or the like also disposes the calibration chart 201 at a position facing the distal end face of the endoscope 2 that is also a position at which the dot at the center of the dot pattern is substantially aligned with the optical axis of the objective optical system 14.

Thereafter, when the power of each portion of the endoscope system 1 is turned on, endoscope information stored in the memory 16 of the insertion portion 11 is outputted to the information processing apparatus 5 through the controller 25.

At a timing that is approximately immediately after the endoscope information that was read out from the memory 16 is outputted to the information processing apparatus 5, the controller 25 performs control with respect to the light source unit 21 to switch the light sources 31a, 31b, and 31c from an "off" state to and "on" state, and also performs control with respect to the driver unit 22 to cause the driver unit 22 to output the first and second driving signals to the actuator 15. Subsequently, as a result of this control by the controller 25, mixed light including R light, G light, and B light is irradiated in a spiral shape onto the surface of the calibration chart 201, return light of the mixed light that was irradiated onto the surface of the calibration chart 201 is received by the light receiving fiber 13, and respective color signals (R signal, G signal, and B signal) that are in accordance with the received return light are sequentially outputted from the detection unit 23.

The controller 25 generates an R image, a G image, and a B image in accordance with the R signal, the G signal, and the B signal outputted from the detection unit 23, and outputs the generated images of each color to the information processing apparatus 5.

In a state in which the coordinate position (0,0) corresponding to the point SA on the XY plane exemplified in FIG. 2 and the position of the dot at the center of the dot pattern that is included in each image outputted from the controller 25 are aligned, the arithmetic processing section 51 acquires the coordinate positions of the respective dots of the dot pattern included in the respective images. That is, the arithmetic processing section 51 that is equipped with a function as a coordinate information acquisition portion acquires the coordinate position of each dot of a dot pattern included in each image outputted from the controller 25, as coordinate information that can identify an irradiation position of illuminating light that is irradiated in a spiral shape from the endoscope 2.

By using pattern matching to measure how much the coordinate positions of dots included in the dot pattern in the G image are shifted in the dot pattern in the R image, the arithmetic processing section 51 calculates, for each pixel of the R image, a color shift amount RZP that shows the size of a color shift of the pixel of the R image relative to a pixel of the G image.

After acquiring the color shift amount RZP for each pixel of the R image which was determined as described above as R image correction information (step S1 in FIG. 9), the arithmetic processing section 51 that is equipped with a function as a correction information acquisition portion outputs the acquired R image correction information to the controller 25 of the main body apparatus 3.

In addition, by using pattern matching to measure how much the coordinate positions of dots included in the dot pattern in the G image are shifted in the dot pattern in the B image, the arithmetic processing section 51 calculates, for each pixel of the B image, a color shift amount BZP that shows the size of a color shift of the pixel of the B image relative to a pixel of the G image.

Subsequently, after acquiring the color shift amount BZP for each pixel of the B image which was determined as described above as B image correction information (step S1 in FIG. 9), the arithmetic processing section 51 that is equipped with a function as a correction information acquisition portion outputs the acquired B image correction information to the controller 25 of the main body apparatus 3.

The controller 25 stores the R image correction information and the B image correction information that is outputted from the information processing apparatus 5 in the memory 24.

Thereafter, the controller 25 generates an R image in accordance with the R signal that is outputted from the detection unit 23, and performs image correction processing based on the R image correction information stored in the memory 24 with respect to the generated R image (step S2 in FIG. 9). Further, the controller 25 generates a B image in accordance with the B signal that is outputted from the detection unit 23, and performs image correction processing based on the B image correction information stored in the memory 24 with respect to the generated B image (step S2 in FIG. 9).

Figure 10:
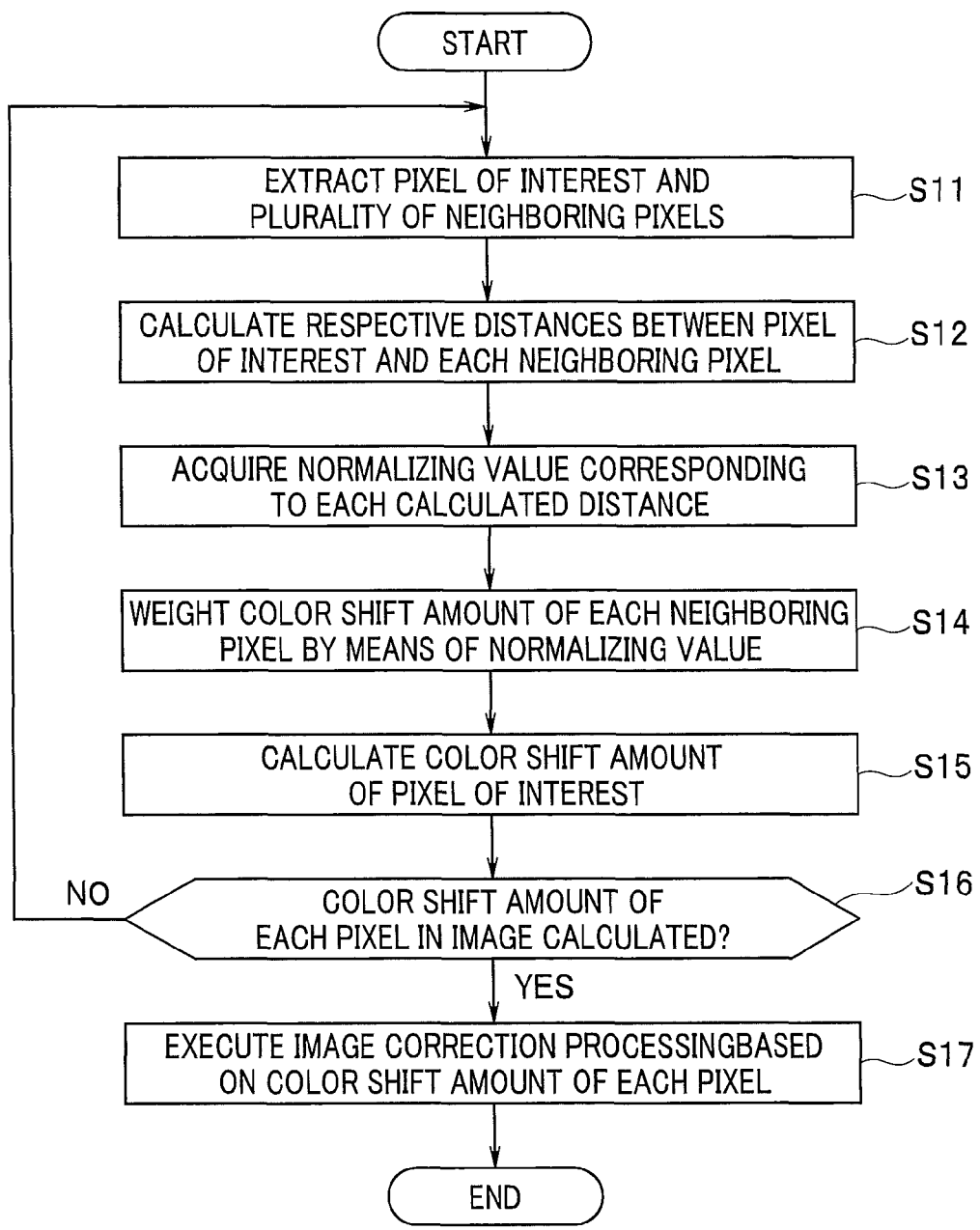
FIG. 10 is a flowchart for describing a specific example of image correction processing that is performed in step S2 in FIG. 9.

A specific example of the image correction processing performed in step S2 in FIG. 9 will now be described taking the case of the R image as an example. FIG. 10 is a flowchart for describing a specific example of image correction processing that is performed in step S2 in FIG. 9.

First, from among the respective pixels in the R image, the controller 25 extracts a pixel of interest as a correction object, and a plurality of neighboring pixels that are positioned in the neighborhood of the pixel of interest (step S11 in FIG. 10).

More specifically, from among the respective pixels in the R image, the controller 25, for example, extracts a pixel of interest PI as a correction object and four neighboring pixels PN1, PN2, PN3, and PN4 that are positioned in the neighborhood of the pixel of interest.

Next, the controller 25 calculates the respective distances between the pixel of interest and each neighboring pixel that were extracted in step S11 in FIG. 10 (step S12 in FIG. 10), and also acquires normalizing values corresponding to the respective distances that were calculated (step S13 in FIG. 10).

More specifically, the controller 25, for example, calculates a distance DP1 between the pixel of interest PI and the neighboring pixel PN1, calculates a distance DP2 between the pixel of interest PI and the neighboring pixel PN2, calculates a distance DP3 between the pixel of interest PI and the neighboring pixel PN3, and calculates a distance DP4 between the pixel of interest PI and the neighboring pixel PN4. In addition, by normalizing so that the total value of the distances DP1 to DP4 calculated as described above becomes 1.0, the controller 25 acquires a normalizing value DN1 corresponding to the distance DP1, a normalizing value DN2 corresponding to the distance DP2, a normalizing value DN3 corresponding to the distance DP3, and a normalizing value DN4 corresponding to the distance DP4, respectively.

The controller 25 weights the color shift amounts of the respective neighboring pixels included in the R image correction information stored in the memory 24 by means of the normalizing values acquired by step S13 in FIG. 10 (step S14 in FIG. 10).

More specifically, based on the R image correction information stored in the memory 24, the controller 25, for example, performs weighting in a manner that multiplies a color shift amount RZPN1 of the neighboring pixel PN1 by the normalizing value DN1, multiplies a color shift amount RZPN2 of the neighboring pixel PN2 by the normalizing value DN2, multiplies a color shift amount RZPN3 of the neighboring pixel PN3 by the normalizing value DN3, and multiplies a color shift amount RZPN4 of the neighboring pixel PN4 by the normalizing value DN4.

Based on the color shift amounts of the respective neighboring pixels that were weighted by step S14 in FIG. 10, the controller 25 calculates the color shift amount of the pixel of interest that was extracted by step S11 in FIG. 10 (step S15 in FIG. 10).

More specifically, as a color shift amount RZPI of the pixel of interest extracted by step S11, the controller 25, for example, calculates a sum total of a value obtained by multiplying the color shift amount RZPN1 by the normalizing value DN1, a value obtained by multiplying the color shift amount RZPN2 by the normalizing value DN2, a value obtained by multiplying the color shift amount RZPN3 by the normalizing value DN3, and a value obtained by multiplying the color shift amount RZPN4 by the normalizing value DN4.

Thereafter, if calculation of the color shift amount RZPI of each pixel in the R image is not completed (step S16 in FIG. 10), the controller 25 repeats the processing from step S11 to step S15 in FIG. 10. When calculation of the color shift amount RZPI of each pixel in the R image is completed (step S16 in FIG. 10), the controller 25 performs image correction processing with respect to the R image based on the calculated color shift amounts RZPI of the respective pixels (step S17 in FIG. 10).

In addition, after performing image correction processing with respect to the B image in a substantially similar manner as the processing performed with respect to the R image by applying the series of processing in FIG. 10, the controller 25 synthesizes, for each frame, the corrected R image and B image on which the image correction processing was performed and an uncorrected G image that is generated in accordance with the G signal outputted from the detection unit 23, and causes the synthesized images to be displayed at a predetermined frame rate on the monitor 4 (step S3 in FIG. 9).

Note that the method of image correction processing described above can also be applied in a substantially similar manner to the objective optical system 14 that has pincushion distortion aberration. More specifically, for example, image correction processing that is substantially the same as the above described image correction processing can be executed by performing processing and the like based on an R image and a B image that include a dot pattern that is drawn so that the diameters of the dots decrease in accordance with the proximity of the dots to an outer edge portion from a center portion of a calibration chart and so that spaces between the dots narrow in accordance with the proximity of the dots to the outer edge portion from the center portion of the calibration chart.

Figure 11:
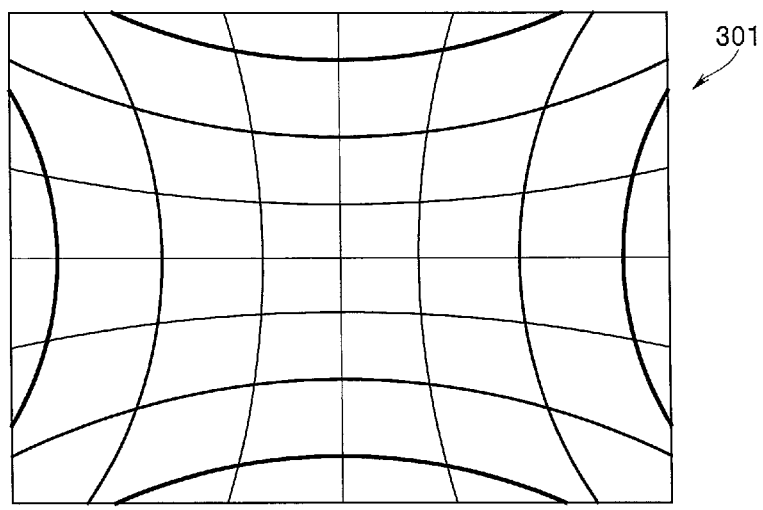
FIG. 11 is a view that illustrates a different example to FIG. 8 of a calibration chart that can be utilized when performing image correction processing.

On the other hand, according to the present embodiment, for example, in a case in which information such as an aberration diagram that can identify the distortion aberration of the objective optical system 14 is included in optical characteristics information, image correction processing may be performed using a calibration chart 301 as shown in FIG. 11 instead of the light irradiation coordinates detection module 101. FIG. 11 is a view that illustrates a different example to FIG. 8 of a calibration chart that can be utilized when performing image correction processing.

The calibration chart 301 is constructed so as to be suitable for the objective optical system 14 that has barrel distortion aberration. As shown in FIG. 11, the calibration chart 301 has a grid pattern including a plurality of grids drawn with black line segments in a region with a white background.

Note that each grid included in the grid pattern in FIG. 11 is drawn so that line widths become thicker in accordance with the proximity of the lines to the outer edge portion from the center portion of the calibration chart 301, the grid spacings widen in accordance with the proximity of the grid spacings to the outer edge portion from the center portion of the calibration chart 301, and the grid shapes become increasingly deformed in accordance with the proximity thereof to the outer edge portion from the center portion of the calibration chart 301.

Image correction processing and the like in a case in which the calibration chart 301 is used will now be described.

First, a surgeon or the like connects the respective portions of the endoscope 2, the monitor 4, and the information processing apparatus 5 to the main body apparatus 3. The surgeon or the like also disposes the calibration chart 301 at a position facing the distal end face of the endoscope 2 that is a position at which the vertex of the center of the grid pattern and the optical axis of the objective optical system 14 are substantially aligned.

Thereafter, when the power of each portion of the endoscope system 1 is turned on, endoscope information stored in the memory 16 of the insertion portion 11 is outputted to the information processing apparatus 5 through the controller 25.

At a timing that is approximately immediately after the endoscope information that was read out from the memory 16 is outputted to the information processing apparatus 5, the controller 25 performs control with respect to the light source unit 21 to switch the light sources 31a, 31b, and 31c from an "off" state to an "on" state, and also performs control with respect to the driver unit 22 to cause the driver unit 22 to output the first and second driving signals to the actuator 15. Subsequently, as a result of this control by the controller 25, mixed light that includes R light, G light, and B light is irradiated in a spiral shape onto the surface of the calibration chart 301, return light of the mixed light that was irradiated onto the surface of the calibration chart 301 is received by the light receiving fiber 13, and respective color signals (R signal, G signal, and B signal) that are in accordance with the received return light are sequentially outputted from the detection unit 23.

The controller 25 generates an R image, a G image, and a B image in accordance with the R signal, the G signal, and the B signal outputted from the detection unit 23, and outputs the generated images of each color to the information processing apparatus 5.

In a state in which the coordinate position (0,0) corresponding to the point SA on the XY plane exemplified in FIG. 2 and the position of the vertex of the center of a grid pattern included in each image outputted from the controller 25 are aligned, the arithmetic processing section 51 acquires the coordinate positions of the respective vertices of the grid patterns included in the respective images. That is, the arithmetic processing section 51 that is equipped with a function as a coordinate information acquisition portion acquires the coordinate position of each vertex of a grid pattern included in each image outputted from the controller 25 as coordinate information that can identify an irradiation position of illuminating light that is irradiated in a spiral shape from the endoscope 2.

By using pattern matching to measure how much the coordinate position of a vertex included in the grid pattern in the G image is shifted in the grid pattern in the R image, the arithmetic processing section 51 calculates, for each pixel of the R image, a color shift amount RZP that shows the size of a color shift of the pixel of the R image relative to a pixel of the G image.

After acquiring the color shift amount RZP for each pixel of the R image which was determined as described above as R image correction information (step S1 in FIG. 9), the arithmetic processing section 51 that is equipped with a function as a correction information acquisition portion outputs the acquired R image correction information to the controller 25 of the main body apparatus 3.

In addition, by using pattern matching to measure how much the coordinate position of a vertex included in the grid pattern in the G image is shifted in the B image, the arithmetic processing section 51 calculates, for each pixel of the B image, a color shift amount BZP that shows the size of a color shift of the pixel of the B image relative to a pixel of the G image.

Subsequently, after acquiring the color shift amount BZP for each pixel of the B image which was determined as described above as B image correction information (step S1 in FIG. 9), the arithmetic processing section 51 that is equipped with a function as a correction information acquisition portion outputs the acquired B image correction information to the controller 25 of the main body apparatus 3.

The controller 25 stores the R image correction information and the B image correction information that is outputted from the information processing apparatus 5 in the memory 24.

Thereafter, the controller 25 generates an R image in accordance with the R signal that is outputted from the detection unit 23, and performs image correction processing based on the R image correction information stored in the memory 24 with respect to the generated R image (step S2 in FIG. 9). Further, the controller 25 generates a B image in accordance with the B signal that is outputted from the detection unit 23, and performs image correction processing based on the B image correction information stored in the memory 24 with respect to the generated B image (step S2 in FIG. 9).

A specific example of the image correction processing performed in step S2 in FIG. 9 will now be described taking the case of the R image as an example.

First, from among the respective pixels in the R image, the controller 25 extracts a pixel of interest as a correction object, and a plurality of neighboring pixels that are positioned in the neighborhood of the pixel of interest (step S11 in FIG. 10).

More specifically, from among the respective pixels in the R image, the controller 25, for example, extracts a pixel of interest PI as a correction object and four neighboring pixels PN1, PN2, PN3, and PN4 that are positioned in the neighborhood of the pixel of interest.

Next, the controller 25 calculates the respective distances between the pixel of interest and each neighboring pixel that were extracted in step S11 in FIG. 10 (step S12 in FIG. 10), and also acquires normalizing values corresponding to the respective distances that were calculated (step S13 in FIG. 10).

More specifically, the controller 25, for example, calculates a distance DP1 between the pixel of interest PI and the neighboring pixel PN1, calculates a distance DP2 between the pixel of interest PI and the neighboring pixel PN2, calculates a distance DP3 between the pixel of interest PI and the neighboring pixel PN3, and calculates a distance DP4 between the pixel of interest PI and the neighboring pixel PN4. In addition, by normalizing so that the total value of the distances DP1 to DP4 calculated as described above becomes 1.0, the controller 25 acquires a normalizing value DN1 corresponding to the distance DP1, a normalizing value DN2 corresponding to the distance DP2, a normalizing value DN3 corresponding to the distance DP3, and a normalizing value DN4 corresponding to the distance DP4, respectively.

The controller 25 weights the color shift amounts of the respective neighboring pixels included in the R image correction information stored in the memory 24 by means of the normalizing values acquired by step S13 in FIG. 10 (step S14 in FIG. 10).

More specifically, based on the R image correction information stored in the memory 24, the controller 25, for example, performs weighting in a manner that multiplies a color shift amount RZPN1 of the neighboring pixel PN1 by the normalizing value DN1, multiplies a color shift amount RZPN2 of the neighboring pixel PN2 by the normalizing value DN2, multiplies a color shift amount RZPN3 of the neighboring pixel PN3 by the normalizing value DN3, and multiplies a color shift amount RZPN4 of the neighboring pixel PN4 by the normalizing value DN4.

Based on the color shift amounts of the respective neighboring pixels that were weighted by step S14 in FIG. 10, the controller 25 calculates the color shift amount of the pixel of interest that was extracted by step S11 in FIG. 10 (step S15 in FIG. 10).

More specifically, as a color shift amount RZPI of the pixel of interest extracted by step S11, the controller 25, for example, calculates a sum total of a value obtained by multiplying the color shift amount RZPN1 by the normalizing value DN1, a value obtained by multiplying the color shift amount RZPN2 by the normalizing value DN2, a value obtained by multiplying the color shift amount RZPN3 by the normalizing value DN3, and a value obtained by multiplying the color shift amount RZPN4 by the normalizing value DN4.

Thereafter, if calculation of the color shift amount RZPI of each pixel in the R image is not completed (step S16 in FIG. 10), the controller 25 repeats the processing from step S11 to step S15 in FIG. 11. When calculation of the color shift amount RZPI of each pixel in the R image is completed (step S16 in FIG. 10), the controller 25 performs image correction processing with respect to the R image based on the calculated color shift amounts RZPI of the respective pixels (step S17 in FIG. 10).

In addition, after performing image correction processing with respect to the B image in a substantially similar manner as the processing performed with respect to the R image by applying the series of processing in FIG. 10, the controller 25 synthesizes, for each frame, the corrected R image and B image on which the image correction processing was performed and an uncorrected G image that is generated in accordance with the G signal outputted from the detection unit 23, and causes the synthesized images to be displayed at a predetermined frame rate on the monitor 4 (step S3 in FIG. 9).

Note that the method of image correction processing described above can also be applied in a substantially similar manner to the objective optical system 14 that has pincushion distortion aberration. More specifically, for example, image correction processing that is substantially the same as the above described image correction processing can be executed by performing processing and the like based on an R image and a B image that include a grid pattern that is drawn so that the line widths become thinner in accordance with the proximity of the lines to the outer edge portion from the center portion of the calibration chart, the grid spacings narrow in accordance with the proximity of the grid spacings to the outer edge portion from the center portion of the calibration chart, and the grid shapes become increasingly deformed in accordance with the proximity thereof to the outer edge portion from the center portion of the calibration chart 301.

That is, as described above, according to the method that performs image correction processing using a predetermined calibration chart that is constructed so as to be suitable for distortion aberration of the objective optical system 14, chromatic aberration of magnification that arises when acquiring an image using a scanning endoscope can be corrected more easily than heretofore.

The present invention is not limited to the above described embodiment, and naturally various changes and applications are possible within a range that does not depart from the spirit and scope of the present invention.

What is claimed is:

1. An endoscope system, comprising:
    an endoscope that includes a light guiding member that guides an illuminating light that is emitted from a light source, an optical system that irradiates the illuminating light that is guided by the light guiding member onto an object, and a drive portion that rocks the light guiding member so that an irradiation position of the illuminating light that is irradiated onto the object through the optical system is an irradiation position along a predetermined scanning pattern;
    a coordinate information acquisition portion that acquires coordinate information that can identify an irradiation position of the illuminating light that is irradiated along the predetermined scanning pattern;
    a storage portion in which optical characteristics information is previously stored that, in a case where light of a predetermined wavelength band is set as a standard of chromatic aberration of magnification that is caused by the optical system, shows a correlation between an image height and an aberration amount of light of another wavelength band;
    a correction information acquisition portion that, upon detecting that the light of the predetermined wavelength band is irradiated onto a position corresponding to a predetermined image height based on the coordinate information, detects an aberration amount of the light of the other wavelength band at the predetermined image height based on the optical characteristics information that is stored in the storage portion, and outputs image correction information that corrects chromatic aberration of magnification of an image that is generated in accordance with return light of the light of the other wavelength band based on the aberration amount; and
    an image processing portion that performs image correction processing based on the image correction information.

2. The endoscope system according to claim 1, wherein the image correction information is a proportion that the aberration amount of the light of the other wavelength band at the predetermined image height occupies with respect to a maximum image height.

3. The endoscope system according to claim 1, wherein the light of the predetermined wavelength band is green light and the light of the other wavelength band is at least one of red light and blue light.

4. The endoscope system according to claim 1, wherein the optical system comprises only an optical member having a positive refractive power.

* * * * *